US006970740B2

(12) United States Patent
Larcom et al.

(10) Patent No.: US 6,970,740 B2
(45) Date of Patent: Nov. 29, 2005

(54) UVC REDIATION THERAPY FOR LEUKEMIA

(75) Inventors: Lyndon L. Larcom, Clemson, SC (US); Amy Tuck, Piedmont, SC (US); Samuel Smith, Greenville, SC (US)

(73) Assignee: Clemson University, Clemson, SC (US)

(*) Notice: Subject to any disclaimer, the term of this patent is extended or adjusted under 35 U.S.C. 154(b) by 0 days.

(21) Appl. No.: 10/609,882

(22) Filed: Jun. 30, 2003

(65) Prior Publication Data

US 2004/0137418 A1 Jul. 15, 2004

(Under 37 CFR 1.47)

Related U.S. Application Data

(63) Continuation-in-part of application No. 09/857,982, filed as application No. PCT/US01/12731 on Apr. 19, 2001, now Pat. No. 6,585,676.
(60) Provisional application No. 60/198,296, filed on Apr. 19, 2000.

(51) Int. Cl.[7] ............................................. A61N 1/30
(52) U.S. Cl. ............................................. 604/20; 604/19
(58) Field of Search ............................................. 604/20

(56) References Cited

U.S. PATENT DOCUMENTS

| 4,428,744 | A | 1/1984 | Edelson |
|---|---|---|---|
| 4,573,960 | A | 3/1986 | Goss |
| 4,613,322 | A | 9/1986 | Edelson |
| 4,831,268 | A | 5/1989 | Fisch et al. |
| 5,147,289 | A | 9/1992 | Edelson |
| 5,712,086 | A | 1/1998 | Horowitz et al. |
| 5,871,459 | A | 2/1999 | Muller |
| 5,980,954 | A | 11/1999 | Bolton |
| 5,984,887 | A | 11/1999 | McLaughlin et al. |
| 6,190,608 | B1 | 2/2001 | Laub et al. |
| 6,193,681 | B1 | 2/2001 | Davidner et al. |
| 6,283,986 | B1 | 9/2001 | Johnson |
| 6,413,714 | B1 | 7/2002 | Margolis-Nunno et al. |
| 6,468,733 | B2 | 10/2002 | Nur et al. |
| 6,569,467 | B1 * | 5/2003 | Bolton ...................... 424/613 |
| 6,585,676 | B1 | 7/2003 | Larcom et al. |

FOREIGN PATENT DOCUMENTS

WO    WO01/80939    1/2001

OTHER PUBLICATIONS

Abstract of Article—*Effect of Deoxynucleosides on the Repair of UV Induced DNA Breaks,* Birgitte MunchPetersen, Purine and Pyrimidine Metabolism in Man IX, Plenum Press, New York, 1998.

(Continued)

*Primary Examiner*—Cheryl Tyler
*Assistant Examiner*—Filip Zec
(74) *Attorney, Agent, or Firm*—Dority & Manning, P.A.

(57) ABSTRACT

Leukocytes from leukemia patients have been found to be readily killed by ultra-violet light-C (UVC) radiation. Cells from healthy donors were minimally affected by doses of UVC 10 times higher than those which caused dramatic drops in the metabolism of diseased cells and eventual death.

Irradiated cells from leukemia patients and from healthy individuals demonstrated a number of single strand DNA breaks and alkali-labile sites compared to unirradiated control cells. The extent of DNA damage to both healthy and diseased cells is dose dependent. However, the diseased cells demonstrated more extensive DNA fragmentation and an inability to undergo self-repair. The heightened sensitivity to UVC radiation of diseased leukocytes from leukemia patients is used to provide an excorporeal treatment of diseased leukocytes followed by the re-introduction of the treated leukocytes to the patient.

9 Claims, 11 Drawing Sheets

| Dose (J/m$^2$) | 4 hours CLL | 24 hours CLL | 48 hours CLL | 4 hours Healthy | 24 hours Healthy | 48 hours Healthy |
|---|---|---|---|---|---|---|
| 0 | 3.0 ± 0.7 | 9.3 ± 2.1 | 21.1 ± 4.8 | 2.8 ± 0.9 | 2.7 ± 0.5 | 4.2 ± 1.1 |
| 2 | 1.0 ± 0.0 | 9.7 ± 5.7 | 31.3 ± 10.9 | - | - | - |
| 4 | 1.8 ± 0.4 | 18.7 ± 2.3 | 43.1 ± 4.1 | 1.2 ± 0.5 | 2.3 ± 1.0 | 3.8 ± 1.1 |
| 8 | 2.9 ± 0.7 | 22.3 ± 1.5 | 47.0 ± 2.4 | 1.7 ± 0.5 | 3.2 ± 1.1 | 4.2 ± 1.4 |
| 16 | 2.4 ± 0.7 | 26.2 ± 3.1 | 50.2 ± 2.1 | 2.2 ± 0.9 | 4.5 ± 2.3 | 9.8 ± 6.0 |
| 24 | 0.8 ± 0.4 | 23.7 ± 4.9 | 44.8 ± 4.2 | 1.3 ± 0.3 | 1.0 ± 0.6 | 1.3 ± 0.3 |
| 32 | 1.0 ± 0.6 | 19.0 ± 4.0 | 39.7 ± 8.9 | - | - | 4.0 ± 2.0 |
| 40 | 0.7 ± 0.7 | 20.7 ± 4.8 | 49.0 ± 2.6 | - | - | - |

OTHER PUBLICATIONS

Abstract of Article—*The Single Cell Gel Assay: A Sensitive Technique for Evaluating Intercellular Differences in DNA Damage and Repair,* R. R. Tice, P. W. Andrews, and N. P. Singh, DNA Damage and Repair in Human Tissues, Plenum Press, New York, 1990, pp. 291–301.

Abstract of Article—*Distribution and Repair of Photolesions in DNA: Genetic Consequences and the Role of Sequence Context,* Evelyne Sage, Photochemistry and Photobiology, vol. 57, No. 1, 1993, pp. 163–174.

Abstract of Article—*Nucleotide Excision Repair,* Aziz Sancar and Moon–Shong Tang, Photochemistry and Photobiology, vol. 57, No. 5, 1993, pp. 905–921.

Abstract of Article—*The comet assay: a comprehensive review,* Daryl W. Fairbairn, Peggy L. Olive, and Kim L. O'Neill, Elsevier Science B.V. Mutation Research 339, 1995, pp. 37–59.

Abstract of Article—*Comet Assay in Human Biomonitoring Studies: Reliability, Validation, and Applications,* Andrew Collins, Mária Dušinská, Michael Franklin, Martina Somorovská, Helena Petrovská, Susan Duthie, Laurence Fillion, Mihalis Panayiotidis, Katarína Rašlová, and Nicholas Vaughan, Environmental and Molecular Mutagenesis 30, 1997, pp. 139–146.

Abstract of Article—*Heterogeneity in Radiation–Induced DNA Damage and Repair in Tumor and Normal Cells Measured Using the "Comet" Assay,* Peggy L. Olive, Judit P. Banáth, and Ralph E. Durand, Radiation Research 122, 1990, pp. 86–94.

Abstract of Article—*Effect of deoxyribonucleosides on the hypersensitivity of human peripheral blood lymphocytes to UV–B and UV–C irradiation,* Michael H.L. Green, Alastair P.W. Waugh, Jillian E. Lowe, Susan A. Harcourt, Jane Cole, and Colin F. Arlett, Elsevier Science B.V. Mutation Research, DNA Repair 315, 1994, pp. 25–32.

Abstract of Article—*Quiescent Human Lymphocytes Do Not Contain DNA Strand Breaks Detectable by Alkaline Elution,* Rick Jostes, Judy A. Reese, James E. Cleaver, Marisa Molero, and William F. Morgan, Experimental Cell Research 182, 1989, pp. 513–520.

Abstract of Article—*Single–strand breaks or alkali–sensitive sites in the DNA of human myeloma plasma cells and chronic lymphocytic leukemia lymphocytes,* L. Brox, A. Ng, E. Pollock, A. Khaliq, and A. Belch, Canadian J. Biochem. Cell, Biol., vol. 63, 1985, pp. 977–981.

Abstract of Article—*Evaluation of Three Methods for the Detection of DNA Single–Strand Breaks in Human Lymphocytes: Alkaline Elution, Nick Translation, and Single–Cell Gel Electrophoresis,* T. Leroy, P. Van Hummelen, D. Anard, P. Castelain, M. Kirsch–Volders, R. Lauwerys, and D. Lison, Journal of Toxicology and Environmental Health, vol. 47, 1996, pp. 409–422.

Abstract of Article—*The Doxyribonucleoside 5'–Triphosphate (dATP and dTTP) Pool in PhytochemagglutininStimulated and Non–Stimulated Human Lymphocytes,* Birgitte Munch–Petersen, Gerda Tyrsted, and B. Dupont, Experimental Cell Research 79, 1973, pp. 249–256.

Abstract of Article—*Ultraviolet–Induced DNA Excision Repair in Human B and Lymphocytes,* Foch F.–H. Yew and Robert T. Johnson, Biochimica et Biophysica Acta, vol. 562, 1979, pp. 240–251.

Abstract of Article—*The effect of deoxynucleosides on repair of DNA breaks in UVC–irradiated human lymphocytes,* M. Holmberg, Elsevier Science Publishers B.V. Mutation Research, vol. 218, 1989, pp. 33–39.

Abstract of Article—*Association of Poly(Adenosine Diphosphoribose) Synthesis and DNA Damage and Repair in Normal Human Lymphocytes,* Nathan A. Berger, Georgina W. Sikorski, Shirley J. Petzold, and Kevin K. Kurohara, J. Clin. Invest., vol. 63, Jun. 1979, pp. 1164–1171.

Abstract of Article—*Inhibition of poly(ADP–ribose)polymerase activity by nucleoside analogs of thymidine,* A.D. Pivazyan, E. M. Birks, T. G. Wood, T. S. Lin, and W. H. Prusoff, Biochem. Pharmacol., vol. 44, No. 5, Sep. 1, 1992, pp. 947–953.

Abstract of Article—*Photopheresis: a clinically relevant immunobiologic response modifier,* R. L. Edelson, Ann. N.Y. Acad. Sci., vol. 636, Dec. 30, 1991, pp. 154–164.

Abstract of Article—*Poly(ADP–ribose) in the cellular response to DNA damage,* N. A. Berger, Radiat. Res., vol. 101, No. 1, Jan. 1985, pp. 4–15.

Abstract of Article—*Ribonucleotide content of mononuclear cells from normal subjects and patients with chronic lymphocytic leukemia: increased nicotinamide adenine dinucleotide concentration in chronic lymphocytic leukemia lymphocytes,* L. F. Liebes, R. L. Krigel, M. Conklyn, D. R. Nevrla, and R. Silber, Cancer Res., vol. 43, No. 11, Nov. 1983, pp. 5608–5617.

Abstract of Article—*The nature of the B lymphocyte in B–chronic lymphocytic leukemia,* F. Caligaris–Cappio, D. Gottardi, A. Alfarano, A. Stacchini, M. G. Gregoretti, P. Ghia, M. T. Bertero, A. Novarino, and L. Bergui, Blood Cells, vol. 19, No. 3, 1993, pp. 601–613.

Abstract of Article—*UV–C Sensitivity of unstimulated and stimulated human lymphocytes from normal and xeroderma pigmentosum donors in the comet assay: a potential diagnostic technique,* M. H. Green, J. E. Lowe, S. A. Harcourt, P. Akinluyi, T. Rowe, J. Cole, A. V. Anstey and C. F. Arlett, Mutat. Res., vol. 273, No. 2, Mar. 1992, pp. 137–144.

Article—*Chronic lymphocytic leukemia lymphoctyes lack the capacity to repair UVC–induced lesions,* Amy Tuck, Samuel Smith, and Lyndon Larcom, Elsevier Science B.V., Mutation Research 459, 2000, pp. 73–80.

Abstract of Article—*Hypersensitivity of Lympyocytes from Chronic Lymphocytic Leukemia Patients to UVC Radiation,* Amy Tuck, Abstracts of the 27th Annual Meeting of the American Society for Photobiology, MPM–E18, 1 page.

Thesis of Amy Tuck entitled "The Sensitivity of Chronic Lymphocytic Leukemia Lymphocytes to Ultraviolet Light–C Due to DNA Repair Defects", dated Aug. 1999.

Bartik, Mary M.; Welker, Debra; & Kay, Neil E.; "Impairments in Immune Cell Function in B Cell Chronic Lymphocytic Leukemia", Seminars in Oncology, vol. 25, No. 1 (Feb) 1998: pp 27–33

Byrd, John C.; Rai, Kanti R.; Sausville, Edward A.: & Grever, Michael R.; "Old and New Therapies in Chronic Lymphocytic Leukemia: Now is the time for a Reassessment of Therapeutic Goals," Seminars in Oncology, vol. 25, No. 1 (Feb.) 1998: pp 65–74.

Byrd, Flinn & Grever, Guest Editors, "Introduction", Seminars in Onvology, vol. 25, No. 1 (Feb.) 1998: pp 4–5.

Wieslthier, Janet S.: Rothstein, Thomas L.; Yu, Thomas L.; Anderson, Tom; Japowicz, Mary C.; & Koh, Howard K.; "Inefficacy of Extracorporeal Photochemotherapy in the Treatment of B–Cell Chronic Lymphocytic Leukemia: Preliminary Results", American Journal of Hematology 41:123–127 (1992).

Pass, Harvey I., "Photodynamic Therapy in Oncology: Mechanisms and Clinical Use," Journal of the National Cancer Institute, vol. 85, No. 6, Mar. 17, 1993, pp. 443–456.

Reed, John C., "Molecular Biology of Chronic Luymphocytic Leukemia," Seminars in Oncology, Vo. 25, No. 1 (Feb.) 1998: pp 11–18.

Tuck, Amy; Smith, Samuel; Whitesides, John F.; & Larcom, Lyndon; "Hypersensitivity of Lympohyctes from Chronic Lymphocytic Leukemia Patients to Ultraviolet Light–C Radiation", Leukemia and Lymphoma, 1999, vol. 36(1–2) pp 169–177.

US/ISA, International Search Report, PCT/US01/12731, 3 pages, Oct. 18, 2001.

Faderl, Stefan & Kantarjian, Hagop M., "Chronic Myelogenous Leukemia and Other Myeloproliferative Disorders", pp. 1–9, Aug. 2000.

Cheson, Bruce D., "Chronic Lymphoid Leukemias and Plasma Cell Disorders", *Scientific American,* pp. 1–9, Apr. 1999.

* cited by examiner

| Dose (J/m²) | 4 hours CLL | 24 hours CLL | 48 hours CLL | 4 hours Healthy | 24 hours Healthy | 48 hours Healthy |
|---|---|---|---|---|---|---|
| 0 | 3.0 ± 0.7 | 9.3 ± 2.1 | 21.1 ± 4.8 | 2.8 ± 0.9 | 2.7 ± 0.5 | 4.2 ± 1.1 |
| 2 | 1.0 ± 0.0 | 9.7 ± 5.7 | 31.3 ± 10.9 | - | - | - |
| 4 | 1.8 ± 0.4 | 18.7 ± 2.3 | 43.1 ± 4.1 | 1.2 ± 0.5 | 2.3 ± 1.0 | 3.8 ± 1.1 |
| 8 | 2.9 ± 0.7 | 22.3 ± 1.5 | 47.0 ± 2.4 | 1.7 ± 0.5 | 3.2 ± 1.1 | 4.2 ± 1.4 |
| 16 | 2.4 ± 0.7 | 26.2 ± 3.1 | 50.2 ± 2.1 | 2.2 ± 0.9 | 4.5 ± 2.3 | 9.8 ± 6.0 |
| 24 | 0.8 ± 0.4 | 23.7 ± 4.9 | 44.8 ± 4.2 | 1.3 ± 0.3 | 1.0 ± 0.6 | 1.3 ± 0.3 |
| 32 | 1.0 ± 0.6 | 19.0 ± 4.0 | 39.7 ± 8.9 | - | - | 4.0 ± 2.0 |
| 40 | 0.7 ± 0.7 | 20.7 ± 4.8 | 49.0 ± 2.6 | - | - | - |

Figure 1

UVC REDIATION THERAPY FOR LEUKEMIA

RELATED APPLICATIONS

This application is a continuation-in-part of U.S. patent application Ser. No. 09/857,982, filed on Jun. 12, 2001 now U.S. Pat. No. 6,585,676, which is a 371 of PCT/US01/12731 filed Apr. 19, 2001, which claims the benefit of U.S. application No. 60/198,296 filed on Apr. 19, 2000, both of which are incorporated herein by reference.

FIELD OF THE INVENTION

This invention is directed towards a therapeutic treatment for diseased leukemic cells. The lymphocytes from chronic lymphocytic leukemia (CLL) and chronic myelogenous leukemia (CML) patients have been found to be sensitive to ultraviolet radiation in the UVC range. It has been found possible to provide UVC radiation exposure which will kill diseased leukocytes from CLL or CML patients without any measurable adverse effects on healthy leukocytes taken from non-leukemia control patients. A treatment therapy in which a patient's blood is treated extracorporeally with UVC radiation is provided which takes advantage of the sensitivity of the CLL lymphocytes or the granulocyte precursors in CML.

BACKGROUND OF THE INVENTION

Chronic lymphocytic leukemia (CLL) is a hematological malignancy characterized by the clonal expansion of naive B-lymphocytes mainly in G0 phase of the cell cycle. CLL results in the accumulation of mature immunologically defective lymphocytes in the G0 phase. The disease is further characterized by the accumulation of B-lymphocytes in bone marrow, lymph nodes, spleen, and liver. In CLL patients, both the B and T cells are ineffective in their response to antigens and are associated with hypogammaglobulinemia and susceptibility to infectious diseases. The end stages of the disease results in the failure of production of myeloid and erythroid marrow elements as well as the presence of lymphoid masses. It is currently believed that the defective lymphocytes in CLL patients are produced at a normal rate as in healthy individuals, but fail to undergo appropriate apoptosis.

Currently, existing therapies and treatment protocols for advanced clinical stages have met with only partial success. Traditional drug treatments have involved combinations of chlorambucil (an alkylating agent) and prednisone (corticoid steroid). More recently, the purine analog fludarabine has been shown to have positive effects on new and pre-treated CLL patients. However, such drug treatments pose undesirable side effects for some patients. Further, some patients develop resistance to a particular drug.

The use of UVA radiation in an extracorporeal photo chemotherapy has been tested in CLL patients and has brought about improvements in T-cell lymphoma patients, but showed no clinical effect in CLL patients. (Wieselthier, J. S. et al *Inefficacy of Extracorporeal Phytochemotherapy in the Treatment of T-cell Chronic Lymphocytic Leukemia: Preliminary Results. American Journal of Hematology*, 41, 123–127 (1992) and (Edelson, R. L. *"Photopheresis: A Clinically Relevant Immunobiologic Response Modifier" ANN NY Sciences*, Vol. 636 p. 154–164 (1991)) and which are both incorporated herein by reference.

CML is a disorder associated with the Philadelphia translocation chromosomal aberration (long arms of chromosomes 9 and 22) and cytogenetic-molecular changes acquired during the clonal disease progression. CML is characterized by the expansion of myeloid progenitor cells at various stages of maturation. Further, the progenitor cells are released prematurely into the circulation system and thereafter accumulate in extramedullary sites such as the spleen. For numerous years, treatment protocols have included therapeutic treatments with bulsafan and hydroxyurea. Both treatments may reduce symptoms, but do not prevent progression of the disease to the blastic phase and resulting patient death. Stem cell transplantation has been successful for qualifying patients. Recently, the drug Gleevic™ has been used as an effective therapy for CML patients with good clinical results. However, drug resistance has been recently reported for some patients taking Gleevic™.

Accordingly, there remains room for variation and improvements with respect to therapies and treatments for leukemia.

SUMMARY OF THE INVENTION

It has now been discovered that a therapeutic treatment for leukemia patients may offer improved efficiencies in alleviating symptoms and offer a useful therapeutic tool in minimizing the onset and severity of symptoms. In so doing, it is possible to avoid chemical drug treatments which may have adverse effects and for which the body may develop resistance In one aspect, the invention resides in a process of treating a leukemia patient by removing a portion of a patient's blood supply; separating the blood supply into a fraction enriched with lymphocytes; exposing the lymphocyte-enriched fraction to UVC radiation; and, returning the treated fraction and untreated fractions to the patient.

In a further aspect, the present invention resides in a method of treating lymphocytes of leukemia patients so as to preclude population accumulation of naïve B-lymphocytes. The use of UVC radiation of the affected population of lymphocytic cells has been found to bring about the cell death of the targeted population of cells through a combination of apoptosis and cell necrosis. In yet another aspect of this invention, it has been found that the levels of UVC radiation needed to bring about the death of the target population of lymphocytic cells is approximately 10% the level required to bring about deleterious effects on healthy lymphocytic cells.

It is another aspect of the present invention to find a method of treating leukocytes of CML patients so as to bring about the targeted cell death of myeloid progenitor cells prematurely released into circulation.

These and other features, aspects, and advantages of the present invention will become better understood with reference to the following description and appended claims.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

FIG. 1 is a table which sets forth a per cent of Trypan blue positive CLL and healthy lymphocytes following UVC radiation.

FIG. 12 is a table of actual and normalized cell counts of Trypan blue positive CML and healthy lymphocytes following UVC radiation.

DESCRIPTION OF THE PREFERRED EMBODIMENT

Figures 2A, 2B:
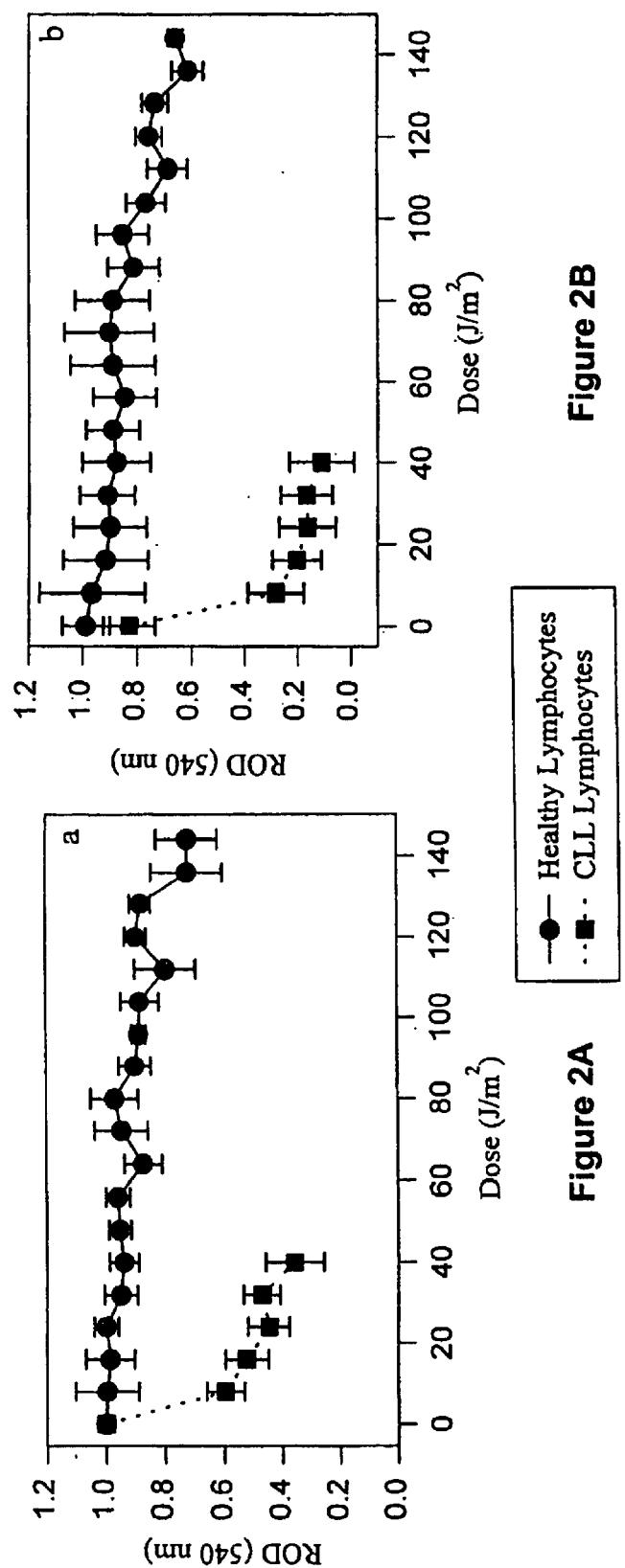
FIG. 2 is comparative graphs of CLL and healthy lymphocytes following irradiation with UVC. The MTT response was measured after 4 hours (a) using 8 CLL patients and 3 healthy control individuals and at 24 hours (b) for 4 CLL patients and 3 healthy control individuals.
Figure 3:
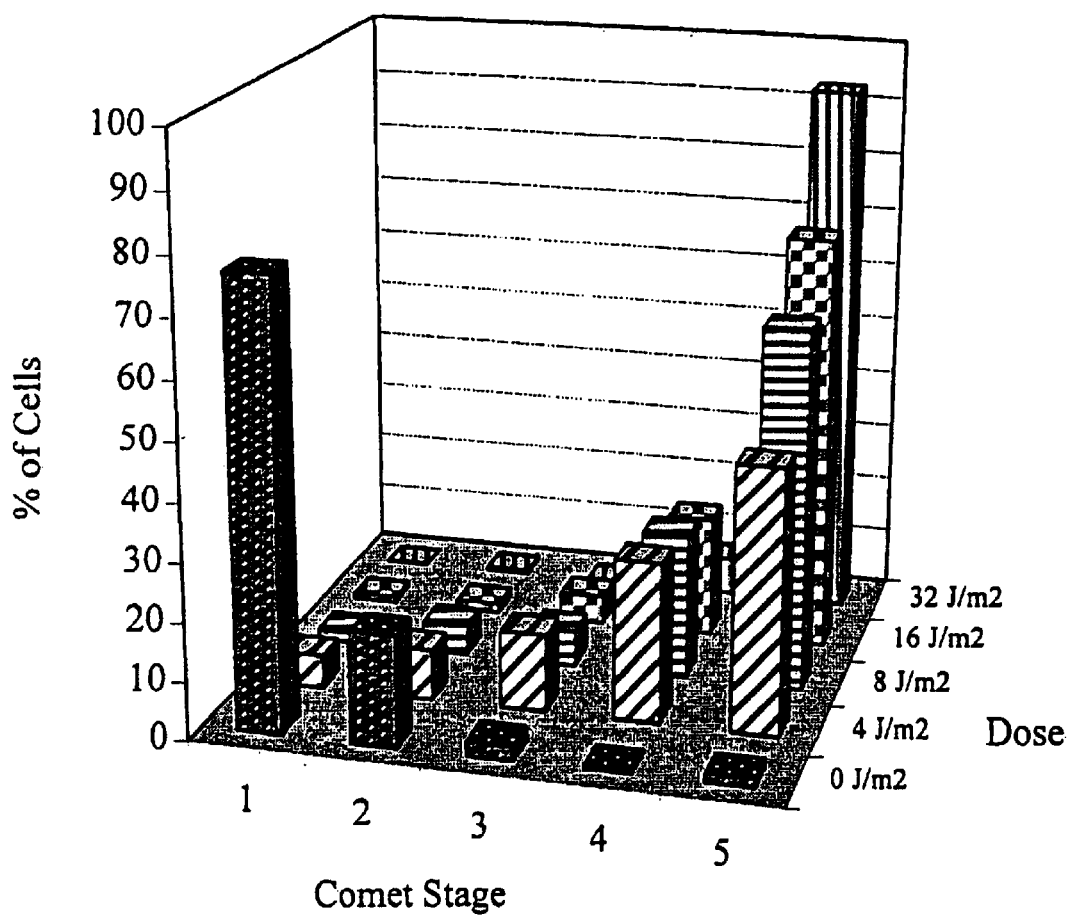
FIGS. 3 and 4 are graphs correlating DNA damage of CLL and healthy lymphocytes following UVC irradiation and an 1 hour incubation as measured by the comet assay.
Figure 4:
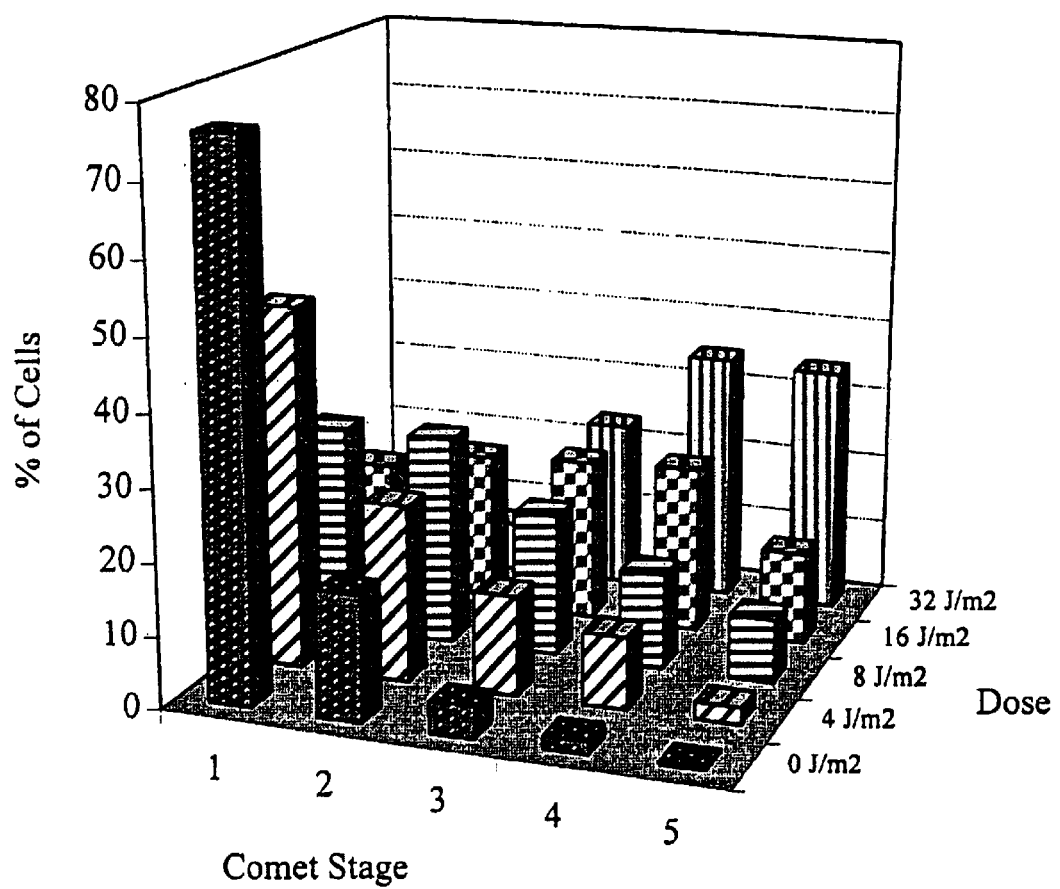

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus, graph or process pathway. To avoid redundancy, detailed descriptions of much of the apparatus once described in relation to a figure is not repeated in the descriptions of subsequent figures, although such apparatus or process is labeled with the same reference numbers.

As used herein, the term "diseased leukocytes" refers to abnormal cell populations associated with one or more forms of leukemia. The term "diseased leukocytes" includes leukocytes associated with chronic lymphoid leukemia such as chronic lymphocytic leukemia (CLL), prolymphocytic leukemia (PLL), hairy-cell leukemia (HCL), and the leukemic phase of non-Hodgkin's lymphomas (NHL). Useful background information with respect to these forms of leukemia may be seen in reference to article entitled, "Chronic Lymphoid Leukemias and Plasma Cell Disorders", by Bruce D. Cheson, M.D., published April, 1999, *Scientific American, Inc.*, Chapter XV, *Lymphoid Leukemias and Plasma Cell Disorders*, pp 1–10, and incorporated herein by reference. The term also includes cells associated with myeloproliferative disorders associated with the pluripotential, hematopoietic stem cells and includes chronic myelogenous leukemia (CML), myeloid metaplasia, and idiopathic myeleofibrosis (MF). Additional background information may be seen in reference to the publication "Chronic Myelogenous Leukemia and Other Myeloproliferative Disorders", by Stefan Faderl, M.D., and Hagop M. Kantarjian, M.D., published August, 2000, *Healtheon/WebMD*, Vol. XVII, *Chronic Myelogenous Leukemia*, pp. 1–9, and which is incorporated herein by reference. Based upon the results reported herein, it is believed that the UVC radiation therapy techniques set forth below are suitable for other forms of leukemia such as acute myelogenous leukemia (AML) which is an acquired (non-inherited) form of leukemia.

In accordance with this invention, it has been shown that the diseased leukocytes of CLL and CML may be killed using doses of UVC radiation substantially lower than those needed to kill or damage healthy lymphocytes. The UVC radiation induces damage at the DNA level by the production of photo lesions that are normally excised by the nucleotide excision repair (NER) system. Using an alkaline comet assay, it has been demonstrated that only limited repair of the UV-induced lesions occurs in the treated CLL cells. In contrast, treated cells from healthy individuals undergo a repair process which is essentially complete within about four hours.

While not wishing to be limited by theory, it is Applicant's belief that the diseased leukocytes from leukemia patients are defective in their ability to regulate utilization and/or synthesis of NAD and ATP following DNA damage. Leukocytes in general are associated with low levels of deoxyribonucleotide pools. The NER process is enhanced when deoxyribonucleosides are added to the medium. This theory is consistent with the observation that the noted defect is consistent with the failure of leukemia cells, such as CLL and CML cells, to undergo a normal apoptotic clearing.

Set forth in the example which follows is the experimental data which establishes the sensitivity of CLL and CML leukocytes to low exposures of UVC radiation. The techniques used and commented on below are well known to one having ordinary skill in the art. Additional information on the experimental protocols may be found in reference to preliminary investigation results reported in a publication by co-inventor Amy Tuck entitled, "The Sensitivity of Chronic Lymphocytic Leukemia Lymphocytes to Ultra-Violet Light-C Due to DNA Repair Defects", dissertation, Clemson University Graduate School, Clemson, S.C., submitted August, 1999, and which is incorporated herein by reference.

Cell Isolation and Culture

Leukocytes from CML patients, CLL patients, and healthy donors were isolated from whole blood on histopaque gradients. The isolated cells were washed in phosphate-buffered saline, pH 7.4 (PBS) and were thereafter suspended in RPMI 1640 medium supplemented with 15% autologous plasma and 1% gentamycin and incubated at 37° C. in an atmosphere of 5% $CO_2$. The cells were irradiated in 1 ml increments at a rate of 1 $W/m^2$. The UVC light source was a germicidal lamp having a maximum intensity at 254 nm.

Lymphocyte Separation

Healthy B-cells were selected from the washed mononuclear cell population using immunomagnetic polystyrene Dynabeads M-450 Pan-B CD 19 (Dynel, Inc.) with the T-cells remaining in suspension. The CLL T-lymphocytes were selected from the lymphocyte population using Dynabeads M-450 CD 4 and CD 8. The purities of the B and T cell populations were measured by flow cytometry using a two color immuno fluorescent agent protocol.

Assay for Cellular Metabolism

Cellular metabolism was measured by the conversion of 3-(4-5-dimethylthiazol-2-yl)-2,5-diphenyl tetrazolium bromide (MTT) to a blue formazan dye or the similar compound of MTS. Following standard incubation assays using the above reagents, absorbance values at appropriate wavelengths were made.

For instance, a sample of $2\times10^5$ cells in a volume of 100 $\mu$l was placed in each well of a 96 well plate along with 25 $\mu$l of a solution of 5 mg/ml MTT. The plates were incubated for four hours at 37° C. and 5% $CO_2$. A lysing solution was then added to each of the wells followed by reading the plate 24 hours later at 540 nm.

Apoptotic Detection

Cell populations were washed in 0.5 ml PBS and then resuspended in 200 $\mu$l Annexin V binding buffer (Caltag). 1 $\mu$g/test of Annexin V was added for apoptosis detection and the solution was allowed to incubate at room temperature for 10 minutes. At least 10,000 cells per tube that fell within the predetermined leukocyte gate were collected in listmode for subsequent analysis. Samples are analyzed on an EPICS 751-flow cytometer with the 488 nm line (300 mw) of an argon ion laser (Model I-90, Coherent) and Clyclops analysis software.

Comet Assay

Cells were incubated for at least one hour to allow the incision step of DNA repair to take place. The cells were then washed and suspended in PBS. $2\times10^4$ cells were mixed with 0.75% low melting point agarose and placed on a base layer of 1.2% normal melting point agarose on a frosted slide. A cover slip was placed on top and the agarose was allowed to gel on ice for 10 minutes. Following removal of the cover slip, a final layer of 0.5% low melting point agarose was placed on top of the second gel layer and the slide was cooled on ice for 10 minutes. The slide was then immersed in a cold lysing solution at 4° C. for a minimum of 1 hour. Next, the slide was soaked in electrophoresis buffer for 20 minutes and electrophoresed at 18 volts and 300 mA for 24 minutes. Following electrophoresis, the slide/cells were washed and stained with propidium iodide for 10 minutes. The propidium iodide (PI) stained comets were examined using inverted fluorescence microscopy and classified into stages as set forth in the accompanying figures.

NAD Enzyme Cycling Assay

The NAD was extracted from cells at the indicated times by boiling in 0.3 mls of 0.1 molar HCl for 5 minutes. The samples were cooled and centrifuged at 2,000 g for 10 minutes. The supernatant was neutralized with 0.1 molar NaOH and re-centrifuged at 10,000 g for 10 minutes and then stored on ice. The enzyme assay was carried out in low light due to light sensitivity of phenazine ethosulfate (PES). Equal volumes of 1.0 M Tricine-NaOH buffer (pH 8.0) and 16.6 mM PES, 4.2 mM 3-(4,5-dimethyl thiazol-2-yl)-2,5-diphenyl tetrazolium bromide (MTT), 40 mM $Na_2$ EDTA, and 5.0 M ethanol were mixed immediately before the assay and 100 $\mu$l were placed in each well of a flat bottom 96 well plate. A standard curve was obtained by taking appropriate volumes of NAD which were added to the wells and the volume in each well was brought to 180 $\mu$l with 0.1 M NaCl. The plate was incubated at 37° C. for 5 minutes. Alcohol dehydrogenase in a concentration of 100 units/ml in 0.1 M Tricine-NaOH was prepared fresh and a volume of 20 $\mu$l was added to each well to start the reaction. Following an incubation of 40 minutes at 37° C., absorbance was read at 595 nm using a microplate reader.

Data Analysis

Data presented in FIGS. 1 through 9 were averaged for the indicated number of donors. In each case, the readings for each experiment were normalized so that the results obtained from different donors could be compared. The NAD concentrations were determined by generating a standard curve. These were then normalized to the concentrations obtained for control cells (unirradiated cells at time 0). Measurements were normalized to the control sample (unirradiated cells) in each experiment. Results are presented as mean±standard error of the mean.

Figure 11:
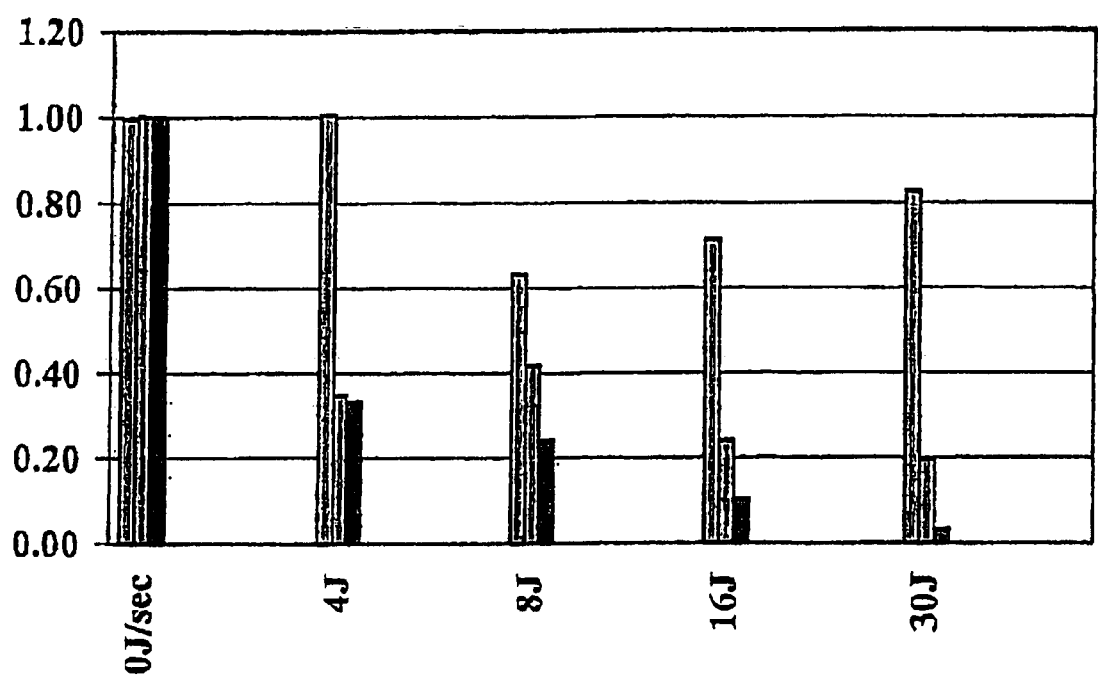
FIG. 11 is a graph of the MTS response of CML lymphocytic populations following UVC irradiation.

Data presented in FIGS. 11 and 12 were taken from a single donor and normalized in reference to the control sample (unirradiated cells) in the experiment.

Extracorporeal UVC Treatment

A variety of suitable methods and apparatuses for exposing blood and blood components to UV light are known within the art. For instance, U.S. Pat. No. 5,871,459 to Miller, U.S. Pat. No. 4,613,322 to Edelson, and U.S. Pat. No. 6,190,608 B1, which are all incorporated herein by reference, are directed to extracorporeal UV irradiation of blood components.

For instance, conventional continuous or batch type centrifuge devices may be used to isolate and enrich fractions of a patient's blood. Further, the centrifuge may be used to isolate a fraction enriched in leukocytes. The red blood cells may be returned to the patient along with a majority of the blood plasma while the concentrated leukocytic fraction is delivered to any one of several types of known irradiation stations.

When combined with a continuous centrifuge, it is possible that between 25 to 75% of a patient's blood lymphocytes may be isolated in a volume of about 250 to 750 ml and contained in a minor proportion of plasma. The patient's outflow of red blood cells and plasma is returned on a continuous basis to the patient. In this manner, a large proportion of the patient's total leukocytes may be treated. Following treatment, the flow of the irradiated enriched lymphocyte fraction can be returned to the patient.

It is noted, however, that it may be desirable to treat only about 10% of a patient's total leukocytes at any one treatment to minimize risks associated with adverse reactions associated with cell necrosis of the UVC treated lymphocytes. An optimal volume/percentage of leukocytes treated for any individual patient may be readily determined by routine experimentation.

While not separately set forth herein, Applicant's investigation has revealed that following UVC exposure to lymphocytes from CLL patients, partial recovery of the treated cells can be achieved through supplementation of media with an external source of deoxyribonuclesides. Accordingly, medium used to suspend the leukocytes during or following UVC treatment should not be supplemented with nucleosides.

The effects of the UVC irradiation on CLL and healthy lymphocytes may be seen in reference to FIG. 1. As set forth in FIG. 1, the UVC treatment induced a significant cell death in CLL cells as indicated by the increase in Trypan blue positive cells. As noted in FIG. 1, at the 24 hour and 48 hour intervals there is a significant increase in cell death above unirradiated controls for UVC doses ranging from 2 to 16 $J/m^2$. The data set forth in FIG. 1 identifies the CLL lymphocytes as being susceptible to low doses of UVC irradiation. In comparison, the healthy lymphocytes are largely unaffected.

As set forth in reference to FIG. 2, UVC irradiation brings about a pronounced effect on cellular metabolism for CLL lymphocytes as measured by reduction of MTT. For CLL lymphocytes, the UVC irradiation produced a dramatic decrease in cellular metabolism. The optical density for cells exposed to 40 J/m$^2$ was 40 to 60% lower than that for unirradiated controls when measured 4 hours after irradiation. This trend continued over 24 hours resulting in a 70 to 80% decrease in absorbance relative to untreated controls. In contrast, after 4 hours following UVC exposure, minimal effects on cells isolated from healthy donors were noted. The minimal effects were noted following UVC doses almost 10 times as great as the exposure levels which caused a significant metabolic drop for CLL cells. While not separately reported, similar effects were noted on other tetrazolium salts MTS and XTT. While the reduction methods may differ for the various salts, all require the presence of NAD(P)H for reduction to take place, thereby indicating a drop in reduced pyridine nucleotides following UVC radiation. The healthy cells did not have a corresponding drop in absorbance as seen in the CLL cell response.

The comet assays are a measurement of single strand breaks and alkaline labile sites when the assays are run at pH's greater than 13. Comet assays are known generally in the art as referenced in the publication by Fairbairn et al, *Mutation Research*, 339, 37–59 (1995) and which is incorporated herein by reference. From a review of the CLL lymphocyte comet data in FIG. 3 with the control data in FIG. 4, it is seen that increasing amounts of UVC radiation will induce greater comet lengths for human lymphocytes, indicating greater amounts of strand breakage. For healthy control cells, there is a gradual shift in the percentage of cells exhibiting higher stages of damage with increasing UVC dose. In contrast, in cells from CLL patients, there is a dramatic increase in DNA damage even at the lowest UVC dose tested of 4 J/m$^2$. As seen in reference to FIG. 3, the unirradiated CLL cells produce comets in stage 1, but after minimal exposure to UV radiation, 73% of the cells produced comets in stages 4 and 5. The comet assay establishes the fact that following UVC irradiation, CLL lymphocytes accumulate single strand breaks to a much greater extent than healthy lymphocytes do. As discussed below, it is believed that the hypersensitivity of CLL lymphocytes to UVC radiation results from the inability of the CLL cells to complete repair of UVC-induced DNA damage. As single strand breaks accumulate, cellular activity brings about a depletion of NAD and ATP, triggering cell death by apoptotic and necrotic mechanisms.

Figure 5A:
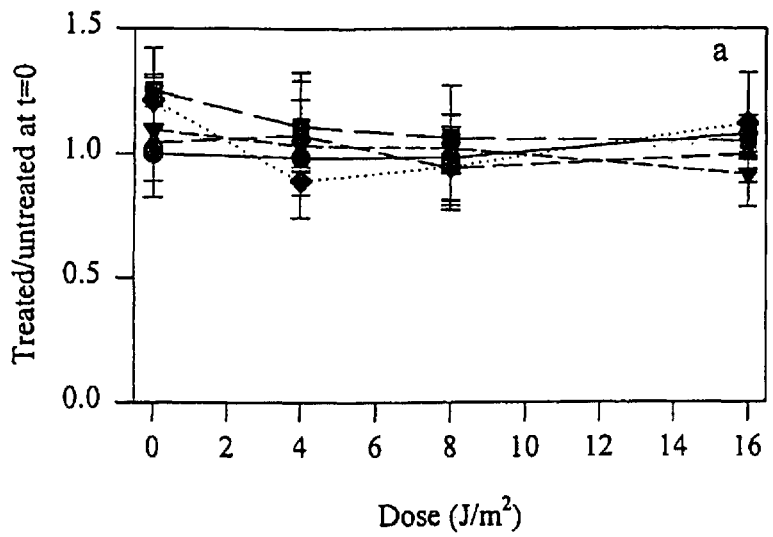
FIG. 5 sets forth graphs indicating changes in NAD concentrations of CLL and healthy lymphocytes following UVC irradiation.
Figure 5B:
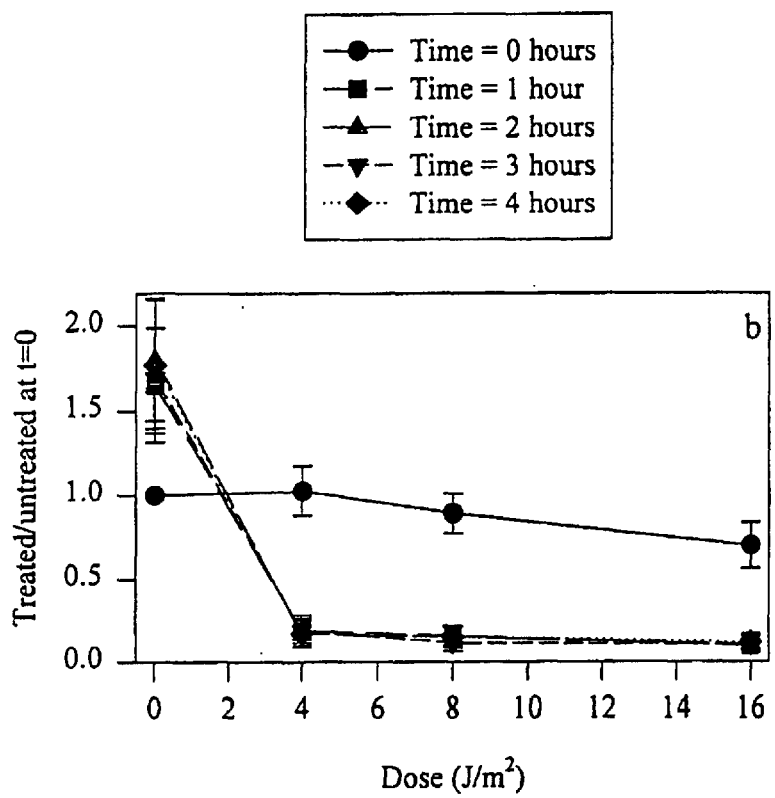

As seen in reference to FIG. 5, changes in NAD concentrations of CLL and healthy lymphocytes were determined following UVC irradiation. For CLL lymphocytes, there was a depletion of NAD at all doses tested. It is believed from literature reports that damage to DNA cells brings about an activation of poly (ADP-ribose) polymerase (PARP) which results in a rapid depletion of NAD following DNA damage. As indicated in FIG. 5, healthy lymphocytes exposed to low dose UVC radiation have no significant decrease in NAD concentration indicating very little PARP activation. In contrast, for CLL lymphocytes, there was depletion of NAD at all doses tested.

While not wishing to be limited by theory, it is believed that a drastic decrease in NAD as reflected above will inhibit ATP production in CLL and other leukemia cells. While not separately reported herein, Applicant's have measured and observed that ATP production is decreased in CLL cells exposed to UVC radiation. It is believed that the decrease in NAD and subsequent ATP production affects energy-dependent processes such as DNA, RNA, and protein synthesis. The inability of the CLL lymphocytes exposed to UVC irradiation to carry out these processes leads to the cell death of CLL lymphocytes. This observation is consistent with literature reports that G0 phase CLL lymphocytes have significantly lower levels of ATP, CTP, UTP, and CDP than lymphocytes from healthy donors. Liebs et al, *Cancer Research*, 43, 5608–5617 (1983). The observation is further consistent with Applicant's unreported work that the effects of UVC radiation on CLL lymphocytes may be mitigated by supplementing the cell medium with deoxyribonucleosides. Accordingly, treatment protocols involving UVC exposure of leukocytes should maintain leukocytes in a non-enhanced medium.

In accordance with this invention, it has been further found that the UVC exposure to CLL lymphocytes results in cell death via a combination of apoptotic and necrotic pathways. Cells from CLL patients and healthy donors were examined for signs of apoptotic and necrotic death by flow cytometry using Annexin V and propidium iodide (PI). Annexin V binds to phosphtidylserine which appears on the outer membrane of a cell in an early stage of apoptosis. Propidium iodide is used to stain the membrane-permeable population of cells.

Figure 6:
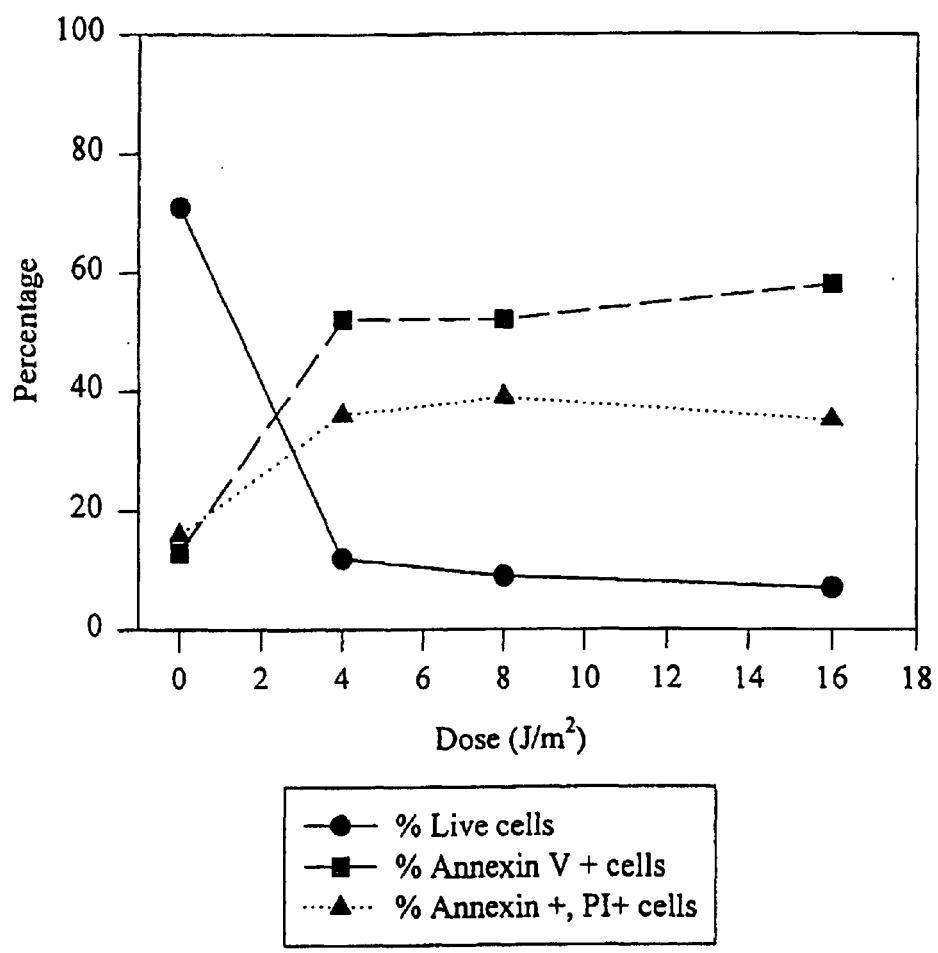
FIGS. 6–8 are graphs setting forth cell death analysis of CLL and healthy lymphocytes following UVC irradiation. Irradiated cells were incubated in 15% autologous plasma TCM for 48 hours and stained with Annexin V and PI followed by examination using flow cytometry.
Figure 7:
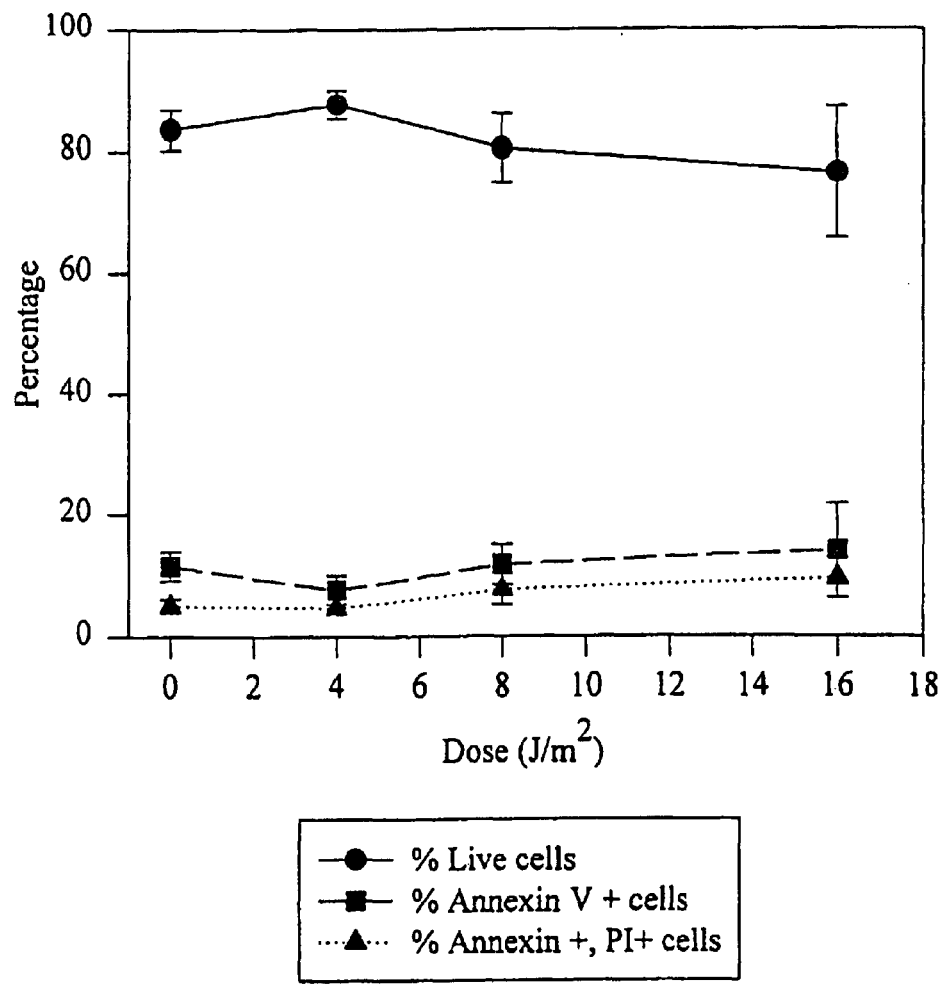
Figure 8A:
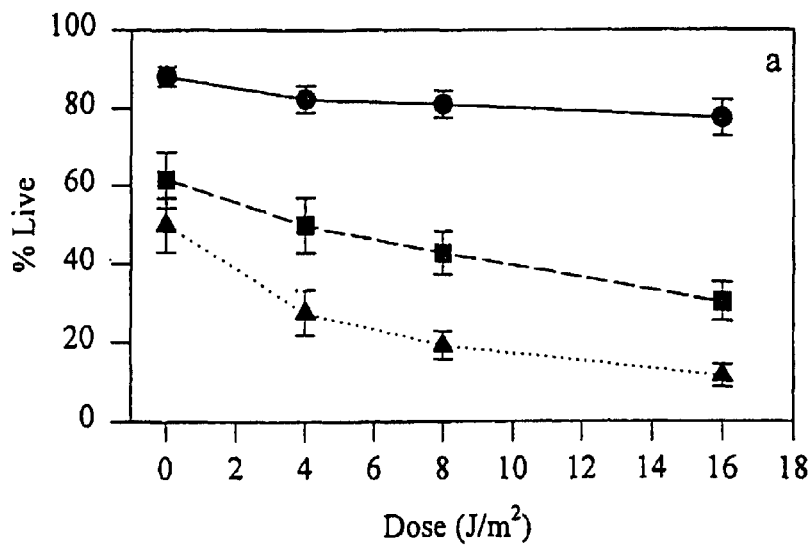
Figure 8B:
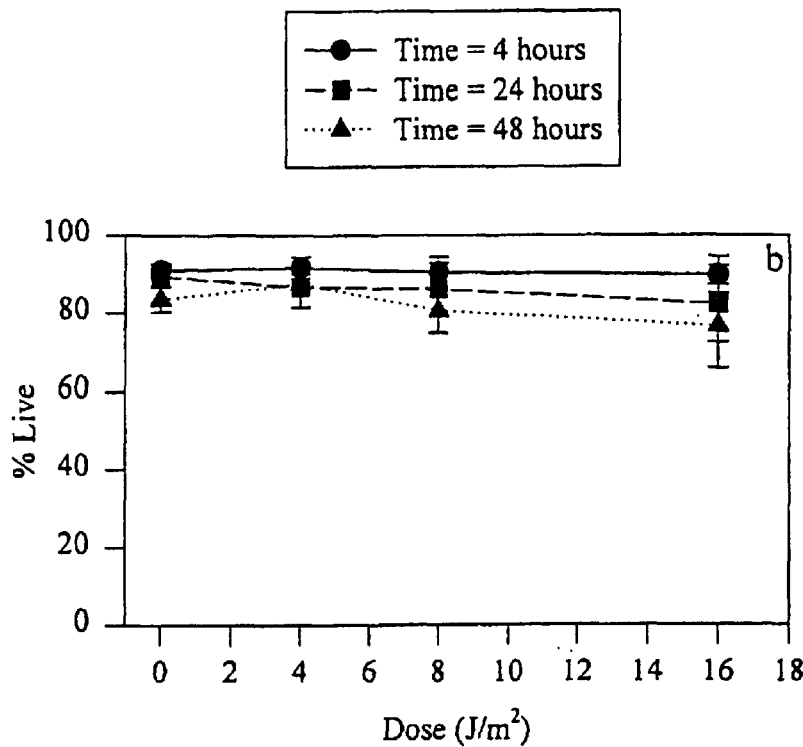

As best seen in reference to FIGS. 6–8, cells which did not stain were considered to be alive. Those cells which stained positively with Annexin V but not with PI, were apoptotic. Those cells which stained positively for both Annexin V and PI were considered necrotic. The data in FIG. 6 is in agreement with the results of Trypan blue staining in FIG. 1, in that cells from CLL patients are significantly more sensitive to killing by UVC. It is further noted that cells having the typical apoptotic morphology characterized by condensed nuclei and smaller size were present in samples containing UVC irradiated cells from CLL patients. However, no cells exhibiting the typical apoptotic morphology were found in samples of the UV-irradiated healthy cells.

Figure 9:
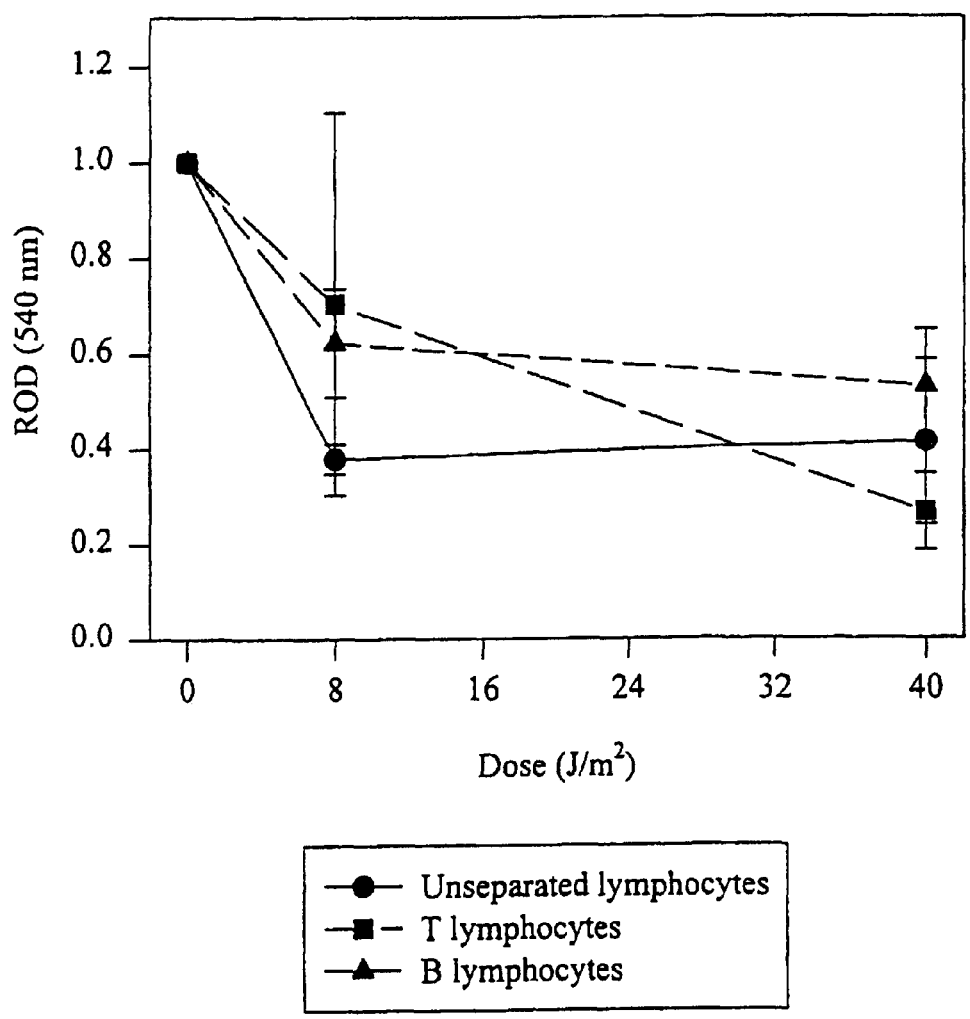
FIG. 9 is a graph of the MTT response of CLL B and T lymphocytic populations following UVC irradiation.

As set forth in FIG. 9, the sensitivity of CLL cells to UVC radiation targets both T-lymphocytes and B-lymphocytes taken from CLL patients. As seen in FIG. 9, when the populations of lymphocytes are segregated as described above to the T-lymphocyte fractions and B-lymphocyte fractions, both fractions show characteristic sensitivity to UVC irradiation as measured by the MTT response.

Set forth in FIG. 11, the leukemic cells from CML patients are significantly more sensitive to UVC-induced death than control populations of leukocytes. As seen in reference to the table of FIG. 12, the CML leukocytes show a dose-dependent sensitivity to UVC radiation.

Based upon the above results, the heightened sensitivity to UVC radiation of leukocytes of CLL and CML patients provides for a therapeutic treatment process which takes advantage of the UVC sensitivity. Using the teachings and methods set forth herein, one of ordinary skill in the art could, without using undue experimentation, readily determine if diseased leukocytes from other forms of leukemia are sensitive to UVC radiation. The present data establishes the effectiveness of UVC radiation on leukemia disorders of both lymphocytic (CLL) and myelocytic (CML) lineages. Given the differences in origin, disease progression, and symptomology these diseases, it is significant that sensitivity to UVC radiation is present in both types of leukemia. Accordingly, it is reasonable to expect that other diseased lymphocytes and leukocytes associated with other forms of leukemia would exhibit similar sensitivity and behavior to UVC radiation exposure.

Figure 10:
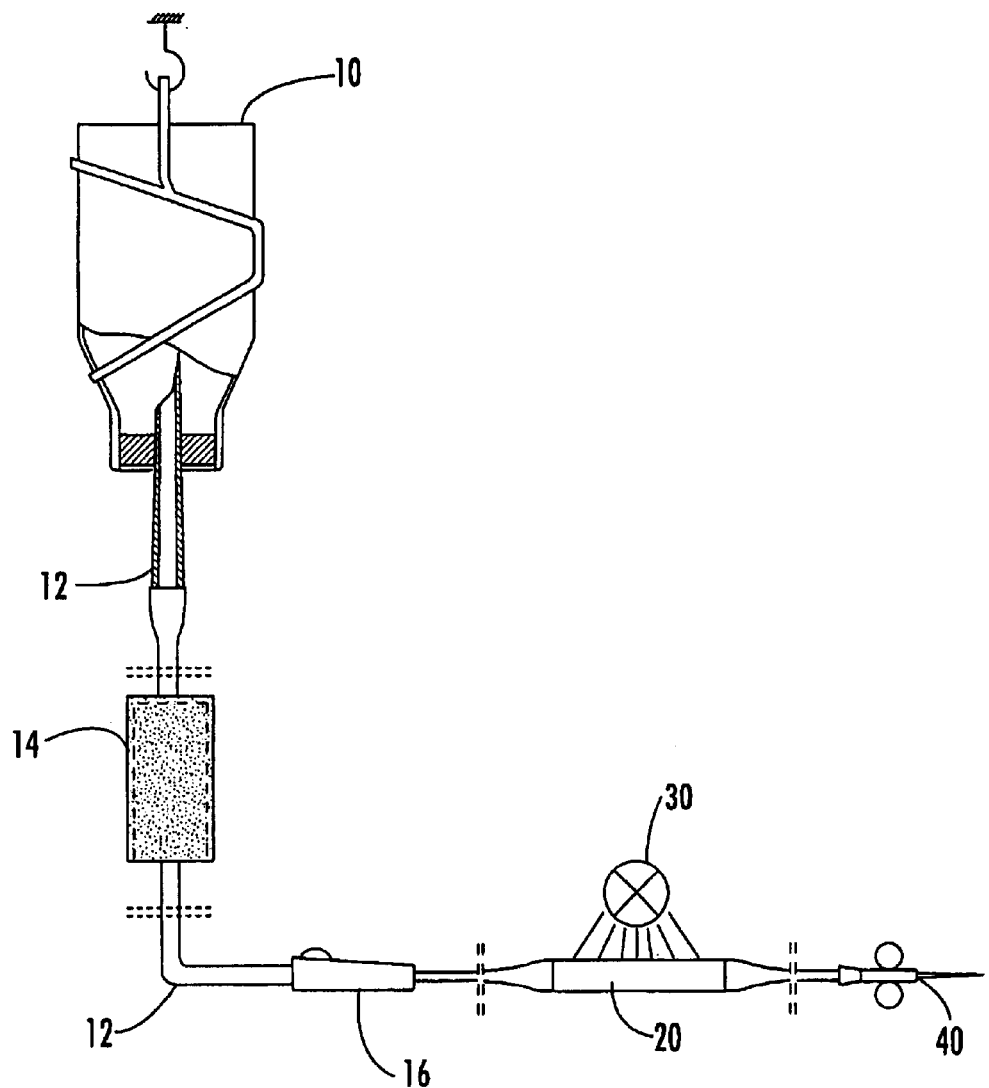
FIG. 10 is a schematic drawing illustrating a method of treating lymphocytes by exposure to UVC radiation.

One suitable treatment method and apparatus can be seen in reference to FIG. 10 in which a supply of leukocytes is present within a container 10. Container 10 may be in the form of a conventional self-contained package of blood products or may be part of a continuous supply conduit from a continuous centrifuge blood treatment apparatus. As further seen in reference to FIG. 10, the leukocyte fraction flows through tubing 12 and may pass through an optional filter 14. An optional roller clamp 16 may be provided for pinching off the conduit tubing 12.

Conduit 12 is in communication with a first end of a quartz tube 20 in which there is a UVC light source 30. As the cells flow through quartz tube 20, the cells are irradiated by the UVC light source 30. Preferably, the emission of the UVC radiation occurs between about 250 to about 270 nm, and more preferably at the wavelength of 254 nm. The preferred irradiation doses received by the CLL lymphocytes are between 1 to 40 $J/m^2$ and more preferably between about 2 to 24 $J/m^2$ and still more preferably between the range of about 4 to 10 $J/m^2$.

For CML leukocytes, effective reduction of living leukocytes can be achieved with UVC exposure at 4 $J/m^2$ and, based upon the CLL data set forth above, a reduction in treated leukocytes can be expected with exposures of around 1 $J/m^2$. As seen in reference to FIG. 11, UVC exposed leukocytes from a CML patient achieve a dramatic reduction at radiation levels of between 4 to 30 $J/m^2$ with noticeable reductions in cell viability in as little as four hours using exposures of between 8 to 30 $J/m^2$. The preferred radiation doses received by the CML leukocytes is preferably between a range of about 4 to about 30 $J/m^2$.

In the method according to the present invention, the irradiation doses and the wavelength used are chosen so that the irradiation doses received by the diseased leukocytes affect the nucleic acids of the diseased leukocytes with minimal disruption of the structure of the peptides or proteins present in the leukocytes or associated plasma. While the example referenced above uses a quartz tube through which the cells are illuminated, other structures such as tubing, bags, glass plates, and other structures may be used. Preferably, the illumination window should be constructed of materials which do not absorb UVC radiation.

Following treatment, the treated leukocytes are removed from a second end of the quartz tube 20 where they may be re-introduced to the patient through a cannula 40.

The advantage of the present treatment protocol is that a significant portion of the diseased leukocytes undergo an apoptotic cell death. As such, the amount of adverse immune reaction associated with the necrotic death pathway is reduced. As such, a larger volume of a patient's leukocytes may be treated at any one time than if all the affected cells underwent an necrotic death.

While it is preferred that initial treatments involve 10% of a patient's total leukocytes at any one interval, the amount may be varied depending upon the patient's subsequent response and tolerance to the treatment process.

It should be appreciated that the present invention does not require the use of any photoactive agents or chemical treatments to bring about the death of the diseased leukocytes. However, it may be possible to combine the present UVC treatment of diseased leukocytes with other conventional drug therapies so as to enhance the treatment of a patient.

It is also understood that the UVC light is but one agent that may be used to bring about a threshold level of DNA damage to diseased leukocytes. Other combinations of light wavelengths, drugs, heat treatments, or other processes which bring about DNA damage may, in accordance with this invention, achieve similar results. For instance, any treatment process which brings about an equivalent damage to the diseased lymphocyte's DNA may be expected to achieve similar mortality of the diseased leukocyte cells given the demonstrated inability of diseased leukocyte cells to undergo repair following damage to the nucleic acids. However, use of UVC light as the initiating agent is preferred in that there have been no observed side effects or detrimental results to healthy leukocytes.

It is also noted that the preferred range of UVC irradiation levels are significantly lower than the ranges used in the past to treat bacterial and/or viral contaminants in excorporeal treatment systems. Applicant's present invention has recognized and demonstrated that the diseased leukocytes have an enhanced sensitivity to UVC irradiation which allows the selective destruction of the diseased leukocytes without compromising the health and viability of non-diseased leukocytes and other cell tissue types.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part. Therefore, the spirit and scope of the appended claims should not be limited to the description of the preferred versions contained therein.

That which is claimed is:

1. A method for reducing the population of diseased leukocytes in patients comprising:
    passing a blood product comprising leukocytes removed from a patient suffering from a disease selected from the group consisting of prolymphocytic leukemia, hairy-cell leukemia, and the leukemic phase of non-Hodgkin's lymphoma past a type C ultra-violet radiation source such that the irradiation dose of ultra-violet radiation received by the leukocytes is within the range of about 1 to about 40 joules/$m^2$.

2. The method according to claim 1 wherein the irradiation dose of UVC radiation received by the leukocytes is between about 1 to about 12 joules/$m^2$.

3. The method according to claim 2 wherein the irradiation dose of UVC radiation is between about 2 to about 10 joules/$m^2$.

4. The method according to claim 1 wherein the UVC radiation occurs at a wavelength around 254 nm.

5. A method for reducing the population of diseased leukocytes in a patient suffering from a myeloproliferative disorder comprising:
    passing a blood product comprising leukocytes removed from a patient suffering from a myeloproliferative disorder past a type C ultra-violet radiation source such that the irradiation dose of ultra-violet radiation received by the leukocytes is within the range of about 1 to about 40 joules/$m^2$.

6. The method according to claim 5 wherein the irradiation dose of UVC radiation received by the blood product is between about 1 to about 12 joules/$m^2$.

7. The method according to claim 6 wherein the irradiation dose of UVC radiation is between about 2 to about 10 joules/$m^2$.

8. The method according to claim 5 wherein the UVC radiation occurs at a wavelength around 254 nm.

9. The method according to claim 5, wherein the myloproliferative disorder is selected from the group consisting of chronic myelogenous leukemia, myeloid meaplasia, idiopathic myeleofibrosis and acute melogeous leukemia.

* * * * *

UNITED STATES PATENT AND TRADEMARK OFFICE
CERTIFICATE OF CORRECTION

PATENT NO.      : 6,970,740 B2
DATED           : November 29, 2005
INVENTOR(S)     : Lyndon L. Larcom, Amy Tuck and Samuel Smith It is certified that error appears in the above-identified patent and that said Letters Patent is hereby corrected as shown below:

<u>Title page, Item [54] and Column 1, line 1,</u>
Title, "REDIATION" should be -- RADIATION --.

Signed and Sealed this

Thirty-first Day of January, 2006

JON W. DUDAS
*Director of the United States Patent and Trademark Office*